(12) United States Patent
Walker et al.

(10) Patent No.: US 9,585,849 B2
(45) Date of Patent: Mar. 7, 2017

(54) BROAD SPECTRUM ANTIVIRAL AND METHODS OF USE

(75) Inventors: Dale M. Walker, Jericho, VT (US); Adriana Elisa Kajon, Albuquerque, NM (US); Vernon E. Walker, Jericho, VT (US)

(73) Assignee: The Burlington HC Research Group, Inc., Jericho, VT (US)

( * ) Notice: Subject to any disclaimer, the term of this patent is extended or adjusted under 35 U.S.C. 154(b) by 1308 days.

(21) Appl. No.: 11/736,471

(22) Filed: Apr. 17, 2007

(65) Prior Publication Data

US 2011/0053894 A1    Mar. 3, 2011

Related U.S. Application Data

(60) Provisional application No. 60/792,738, filed on Apr. 17, 2006.

(51) Int. Cl.
    *A61K 31/13*      (2006.01)
    *A61K 31/66*      (2006.01)
    *A61K 31/661*     (2006.01)

(52) U.S. Cl.
    CPC .............. *A61K 31/13* (2013.01); *A61K 31/66* (2013.01); *A61K 31/661* (2013.01)

(58) Field of Classification Search
    CPC ........................... A61K 31/145; A61K 31/661
    USPC ................................................. 514/131, 665
    See application file for complete search history.

(56) References Cited

U.S. PATENT DOCUMENTS

| | | | |
|---|---|---|---|
| 5,424,471 A | 6/1995 | Kennedy et al. | |
| 5,591,731 A | 1/1997 | Kennedy et al. | |
| 5,804,571 A | 9/1998 | Schein | |
| 5,824,664 A | 10/1998 | Schein | |
| 5,994,409 A | 11/1999 | Stogniew et al. | |
| 6,489,312 B1* | 12/2002 | Stogniew et al. | 514/109 |
| 2002/0132795 A1 | 9/2002 | Stogniew et al. | |
| 2004/0247627 A1 | 12/2004 | Nguyen-Xuan | |
| 2009/0239817 A1 | 9/2009 | Walker et al. | |
| 2013/0337046 A1 | 12/2013 | Walker et al. | |

FOREIGN PATENT DOCUMENTS

| | | |
|---|---|---|
| WO | 90/14007 A1 | 11/1990 |
| WO | WO 94/22307 | 10/1994 |
| WO | WO 01/08662 | 2/2001 |
| WO | WO 2007/123868 | 11/2007 |

OTHER PUBLICATIONS

Kalebic et al. "Organic thiophosphate WR-151327 suppresses expression of HIV in chronically infected cells," AIDS REsearch and Human Retrovirus, 1994, vol. 10, No. 6, pp. 727-733.*
Cai et al. "Inhibition of influenza infection by glutathione," Free Radical biology & Medicine, 2003, vol. 34, No. 7, pp. 928-936.*
Eckburg et al. "Avian influenza in Humans: A practical review for Clinicians," Infections in Medicine, 2005, vol. 22, No. 11, pp. 535-542.*
Stephenson "New HIV prevention strategies urged," JAMA, 2004, vol. 292, No. 10, pp. 1163-1164.*
Grdina et al. "Relationship between cytoprotection and mutation prevention by WR-1065," Military Medicine, 2002, vol. 167, Suppl. 1, pp. 51-53.*
Giannopoulou et al. "amifostine has antiangiogenic properties In vitro by changing the redox status of human endothelial cell s," Free Radical REsearch, 2003, vol. 37, No. 11, pp. 1191-1199.*
Khoo et al. "Adenovirus infections in human immunodeficiency virus-positive patients:Clinical features and molecular epidemiology," The Journal of Infectious Diseases. 1995, vol. 172, No. 3, pp. 629-637.*
Allegra et al., 2002, Amino Acids 22(2):155-166.
Bergamini et al., 1996, J. Infect. Dis. 174(1):214-218.
Brekken et al., 1998, J. Biol. Chem. 273(41):26317-26322.
Clark et al., 1997, Cancer Epidemiol. Biomarkers and Prevention 6:1033-1037.
Cremisi, 1979, Microbiol. Rev. 43(3):297-319.
Gai et al., 2004, Cell 119(1):47-60.
Grdina et al., 2000, Drug Metabol. Drug Interact. 16(4):237-279.
Gutschow et al., 1995, Pharmazie 50(10):672-675.
Hamasaki et al., 2001, Bioorg. Med. Chem. Lett. 11(4):591-594.
Ho et al., 1995, AIDS Res. Hum. Retroviruses 11(4):451-459.
Kalebic et al., 1994, AIDS Res. Hum. Retroviruses 10:727-733.
Kellenberger, 1988, Biophys. Chem. 29(1-2):51-62 (Abstract Only).
Laayoun et al., 1994, Int. J. Radiat. Biol. 66(3):259-266.
Lacourciere et al., 2000, Biochemistry 39(19):5630-5641.
Li et al., 2001, Biochemistry 40(5):1150-1158.
List et al., 1997, Blood 90(9):3364-3369.
Luedtke et al., 2003, Biopolymers 70(1):103-119.
Newton et al., 1996, Radiat. Res. 146(2):206-215.
Nguyen et al., 2003, Anticancer Research 23:1649-1656.
Nishizono et al., 2000, Nucleosides Nucleotides Nucleic Acids 19(1-2):283-295.
North et al., 2002, Mol. Carcinog. 33(3):181-188 (Abstract Only).
Oiry et al., 2004, J. Med. Chem. 47(7):1789-1795.
Olsen et al., 1990, Genes Dev. 4(8):1357-1364.
Perno et al., 1988, J. Exper. Med. 168:1111-1125.
Qian-Cutrone et al., 1996, J. Nat. Prod. 59(2):196-199.
Rasey et al., 1984, Radiat. Res. 97(3):598-607 (Abstract Only).
Rasey et al., 1988, Pharmacol. Ther. 39(1-3):33-43.
Reddy et al., 1999, Rev. Nat. Med. 5(6):635-642.
Rossio et al., 1998, J. Virol. 72:7992-8001.
Santini et al., 1999, Haematologica 84(11):1035-1042.
Schuchter, 1996, Semin. Oncol. 23(4) Suppl. 8:40-43.
Xiao et al., 2001, Bioorg. Med. Chem. 9(5):1097-1113.
Zang et al., 1999, Virology 259(2):299-304.
Zapp et al., 1997, Bioorg. Med. Chem. 5(6):1149-1155.
Aquaro et al., 1988, J. Med. Virol. 68:479-488 (Abstract Only).

(Continued)

*Primary Examiner* — Shengjun Wang
(74) *Attorney, Agent, or Firm* — LeClairRyan, a Professional Corporation

(57) ABSTRACT

A method for the prevention or treatment of Influenza virus infection or Adenovirus infection by administering an effective amount of a compound of Formula (I), Formula (II), or similar compound to an individual in need is provided.

17 Claims, No Drawings

(56) References Cited

OTHER PUBLICATIONS

Berry et al., 2004, Surg. Oncol. Clinics N. Amer. 174(1):214-218 (Abstract Only).
Calabro-Jones et al., 1998, Rad. Res. 149:550-559 (Abstract Only).
Capizzi, 1996, Eur. J. Cancer 32A(Suppl. 4):S5-S16 (Abstract Only).
Freireich et al., 1966, Cancer Chemother. Rep. 50(4):219-244.
Geary et al., 1989, Res. Commun. Chem. Pathol. Pharmacol. 65(2):147-159 (Abstract Only).
Hoffmann et al., 2001, Environ. Mol. Mutagen. 37:117-127 (Abstract Only).
Kalebic et al, 1991, Proc. Natl. Acad. Sci. USA 88:986-990.
Maestra et al., 2000, Clin. Exper. Immunol. 119:123-129.
Nogrady, 1985, Medicinal Chemistry, A Biochemical Approach, Oxford Ujniversity Press, New York, pp. 388-392.
Ozcan Arican, 2005, Cancer Chemother. Pharmacol. 56(2):221-229 (Abstract Only).
Poirier et al., 2004, Toxicol. Appl. Pharmacol. 199:151-161 (Abstract Only).
Simon et al., 1994, Chemico-Biological Interactions 91:217-224 (Abstract Only).
Smoluk et al., 1986, Rad. Res. 107(2):194-204 (Abstract Only).
UNAIDS/WHO, Dec. 2005, AIDS Epidemic Update: Special Report on HIV Prevention, 92 pages.
Weissman et al., 1993, Proc. Natl. Acad. Sci. USA 90:2537-2541.
Woloschak et al., 1995, Cancer Res. 55:4788-4792.
International Search Report for PCT/US2007/009234, 2007.
International Preliminary Report on Patentability and Written Opinion for PCT/US2007/009234, 2007.
Information Disclosure Statement Filed on or about Jul. 7, 2009 in U.S. Appl. No. 12/297,310.
Kaul et al., "Dose proportionality of stavudine in HIV seropositive asymptomatic subjects: application to bioequivalence assessment of various capsule formulations," Biopharm Drug Dispos. 16(2):125-36 (1995).
Restriction Requirement, U.S. Appl. No. 12/297,310, 7 pages (mailed Aug. 16, 2011).
Office Action, U.S. Appl. No. 12/297,310, 7 pages (mailed Nov. 2, 2011).
Office Action, U.S. Appl. No. 12/297,310, 8 pages (mailed Jan. 30, 2014).
Sgarbanti et al., "Intracellular Redox State as Target for Anti-Influenza Therapy: Antioxidants Always Effective?," Curr. Topics Med. Chem. 14:2529-2541 (2014).
Davidson et al., "Biological Characteristics of Some Improved Radioprotectors," in Radiation Sensitizers: Their Use in the Clinical Management of Cancer 309-320 (L.W. Brady ed., Masson Pub., 1980).
Grdina et al., "Radioprotectants: Current Status and New Directions," Dept. of Rad. and Cell. Oncology, The University of Chicago 63(suppl 2)2-10 (2002).

* cited by examiner

BROAD SPECTRUM ANTIVIRAL AND METHODS OF USE

CROSS-REFERENCE TO RELATED APPLICATIONS

This application claims priority to and the benefit of the filing of U.S. Provisional Patent Application Ser. No. 60/792,738, entitled "Broad Spectrum Antiviral and Methods of Use", filed on Apr. 17, 2006, and the specification and claims thereof are incorporated herein by reference.

FIELD OF THE INVENTION

A method for the prevention or treatment of DNA viruses, RNA viruses, and DNA and RNA reverse transcribing viruses infection by administering an effective amount of a compound of Formula (I), Formula (II) or a derivative thereof to an individual in need is provided.

BACKGROUND OF THE INVENTION

Viruses can be divided into several (arbitrary) classifications based upon the type of nucleic acid that they carry and the mode of expression. Table 1 illustrates one classification scheme based upon "The International Code of Virus Classification and Nomenclature", and the classification system developed by Dr. David Baltimore (incorporated herein by reference)

is an urgent need for broad spectrum antiviral drugs that can be used in mono- or combined therapy to treat the numerous viral diseases caused by DNA viruses, RNA viruses and DNA and RNA reverse transcribing viruses for which limited or no therapeutic options are currently available. The demand for new effective and safe antiviral strategies has become an increasingly important problem to solve in recent years due to the rising prevalence of chronic viral infections such as HIV and hepatitis B and C, the emergence of new viruses or viral strains such as the SARS coronavirus and pathogenic Avian Influenza strains, the ever-present threat of viral pandemics from agents like virulent strains of influenza A, and the potential danger of hemorrhagic fever viruses and eradicated viruses such as variola virus being exploited as bioterrorist weapons.

A limited number of chronic viral diseases, which affect millions of people world-wide (e.g., 40 million individuals are HIV-infected), can be controlled to some degree, but no cures are currently available. As a result, infected individuals provide a reservoir for the respective virus through which naïve individuals become infected, thereby, perpetuating the problem of viral infection of significant human populations with these pathogens. Currently available antiviral drugs, such as the nucleoside reverse transcriptase inhibitors (NRTIs) used to inhibit viral replication of specific pathogenic viruses, have resulted in recognizable improvements in the ability to control infections with these pathogens and to improve the quality and length of life of infected indi-

TABLE 1

| Group Name | Nucleic Acid Type | Order | Examples |
| --- | --- | --- | --- |
| DNA viruses | Double stranded DNA viruses | Order: Caudovirales | Ex. Enterobacteria phage T4 |
| | | Unassigned viruses | Ex. Family Adenoviridae |
| | | | Ex. Family Herpesviridae |
| | | | Ex. Family Polymaviridae (simiam virus 40) |
| | | | Ex. Family Poxviridae (Cowpox virus, Variola virus-smallpox) |
| | Single stranded DNA viruses | Unassigned bacteriophages | |
| | | Unassigned viruses | Ex. Family Parvoviridae |
| RNA viruses | Double stranded RNA viruses | Unassigned viruses | Ex. Family Reoviridae |
| | (+) single-stranded RNA or mRNA-like viruses | Order: Nidovirales | Ex. Family Coronaviridae (coronavirus, SARS) |
| | | Unassigned viruses | Ex. Family Flaviviridae (Yellow fever virus, West Nile virus, Hepatitis C virus) |
| | | | Ex. Family Picornaviridae (poliovirus, rhino virus, hepatitis A virus) |
| | | | Ex. Togaviridae (Rubella virus) |
| | (−) single-stranded RNA viruses | Order: Mononegavirales (non-segmented negative stranded viruses) | Ex. Family Paramyxoviridae (measles virus, mumps virus) |
| | | | Ex. Family Rhabdoviridae (rabies virus) |
| | | Segmented negative stranded viruses | Ex. Family Orthomyxoviridae (Influenza viruses) |
| DNA and RNA reverse transcribing viruses | Single-stranded RNA reverse transcribing viruses | Unassigned viruses | Ex. Family Retroviridae (Retroviruses, HIV) |
| | Double-stranded DNA reverse transcribing virus | Unassigned viruses | Ex. Family Hepadnaviridae (Hepatitis B virus) |

The design and discovery of new antiviral drugs can be directed against either viral or cellular targets. Drugs that inhibit viral proteins are more likely to be virus-specific and are more prone to the development of resistance. Thus, there viduals. A partial list of currently available antiviral drugs used to inhibit viral replication of specific pathogenic viruses is provided in Appendix 2 (for eg. the NRTIs). The therapies listed have resulted in recognizable improvements in the ability to control infections from these pathogens and to improve the quality and length of life of infected individuals. However, currently available classes of antiviral agents have limited utilities due to their narrow scope of activities against different viruses and/or problems with significant drug-induced toxicities. In addition, the modes of action of the NRTIs and other drugs in current clinical use predispose to the development of drug resistance through viral mutations. Finally, many currently available drugs have considerable side effects that prevent their wide spread use to achieve treatment or prevention goals.

SUMMARY OF THE INVENTION

There is a clear need for new antiviral agents and combination therapies to suppress diseases caused by DNA viruses, RNA viruses and DNA and RNA reverse transcribing viruses. The compositions and methods of the preferred embodiments provide such agents and associated methods of treatment.

Amifostine is a pro-drug that is metabolized by alkaline phosphatase to the reduced free thiol (WR-1065); oxidation of WR-1065 leads to formation of the disulfide (WR-33278). These reactions can be depicted schematically as follows:

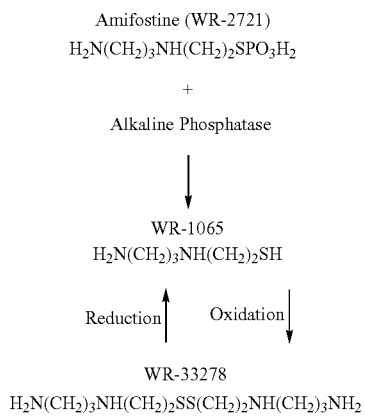

Structural similarities can be observed between spermine (chemical formula $H_2N(CH_2)_3NH(CH_2)_2(CH_2)_2NH(CH_2)_3NH_2$) and WR-1065 and WR-33278. Spermine is associated with nucleic acids and is thought to stabilize helical structure, particularly in viruses. WR-1065 appears to function as an analog of the polyamine spermine, and to compete with spermine for sites on DNA, and probably also on other nucleic acids and proteins. Thus, analogs of WR-1065 and the other compounds of preferred embodiments, as discussed below, may function as spermine or other polyamine analogs, and may mimic the antiviral and polyamine-like activity of WR-1065.

Thiol metabolites of amifostine are believed to be responsible for most of the cytoprotective and radioprotective properties of amifostine. Amifostine is taken up by cells through a combination of passive and active transport processes where it is metabolized to its active forms; these metabolites participate in a number of functions. These functions include, but are not limited to, (i) protection against radiation induced cytotoxicity and cell killing, (ii) protection against radiation-induced mutagenesis/carcinogenesis, (iii) modulation of topoisomerase I and topoisomerase II alpha activities, (iv) modulation of conformational changes in chromatid structure, (v) inhibition of cell cycle progression, (vi) inhibition of endonuclease activity, (vii) competition with spermine in polyamine transport systems, (viii) induction and repression of gene expression (effect dependent upon the particular gene). Other activities include detoxifying cisplatin and other alkylating agents, scavenging free radicals, modulating apoptosis, and modifying the activity of specific enzymes/proteins.

To better understand their radioprotective activity, pharmacokinetic studies of amifostine and phosphonol have been performed; because of the stated goal of the studies, tissues known to be sensitive to radiation-induced damage were evaluated most extensively. The results have shown that the drugs are distributed to most normal tissues and to a lower degree to tumor tissue. The highest levels of drug distribution occurred in the following tissues/organ systems (in order from highest to lowest): kidney, liver, salivary gland, heart, spleen, lung, muscle, and brain (bone marrow was also referred to as having high levels, but levels relative to other tissues are not given) (Rasey et al. 1988, *Pharmac Ther.* 39: 33-43). It has further been demonstrated that certain normal tissues are especially effective at uptake of the drugs (and/or their metabolites) and retention of those metabolites; these tissues include: kidney, liver, salivary gland, and lung (Rasey et al., (1984), *Radiat. Res.* 97(3): 598-607). It is possible that other tissues that have not been tested also perform like the above mentioned tissues. These studies establish the ability to obtain therapeutic levels of these drugs and/or their metabolites in the cells of these tissues/organ systems. Therapeutic drug levels are also expected to be obtained in tissues or organs systems where drug pharmacokinetics resemble that of the above mentioned tissues.

Studies with amifostine incorporated into nanoparticles have shown that this preparation technique constitutes an effective mechanism for delivering amifostine to multiple organ systems over a prolonged time period. There was no significant difference in survival of bone marrow progenitor cells in mice treated with 500 mg/kilogram amifostine by either IP injection or by nanoparticles (administered by gavage, equivalent to oral dosing in humans) one hour prior to a dose of 8 to 9 Gy whole-body gamma irradiation. These studies also showed significant protection of jejunal crypt cells following the same exposures. Pharmacokinetic studies of amifostine distribution and retention in a variety of tissues following oral administration of PLGA/amifostine nanoparticles showed high levels of retention in all evaluated tissues 30 minutes after administration. Retention of drug four hours after administration was demonstrated in the following tissues (in order from highest to lowest): liver, jejunum, stomach, ileum, duodenum, bone marrow, and spleen.

The cytoprotective effects of amifostine appear to be dependent upon a number of factors including, but not limited to, oxygen tension, pH, gene status (including the presence of a functional p53 gene), and enzyme status (including the expression of alkaline phosphatase in the cell membrane). Differences in these factors appear to be responsible for the differential cytoprotective effect mediated by amifostine between tumor cells and normal, nontumorigenic tissue.

According to one aspect amifostine, phosphonol and their derivatives and analogs are particularly effective in inhibiting replication of DNA viruses, RNA viruses, and DNA and RNA reverse transcribing viruses.

Accordingly, in a first aspect a method of treating or preventing a DNA virus, a RNA virus and/or a DNA or RNA reverse transcribing virus infection in an individual in need thereof is provided, comprising the step of administering to the individual an effective antiviral amount of a compound or a pharmaceutically acceptable salt or solvate thereof, wherein the compound comprises Formula (I) or Formula (II)

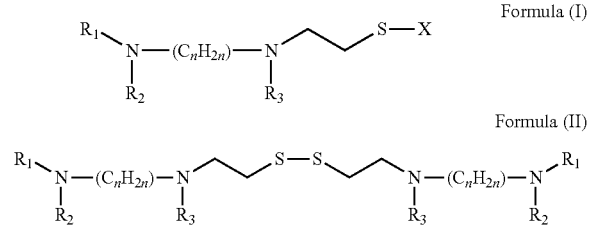

or a pharmaceutically acceptable salt or solvate thereof, wherein X is selected from the group consisting of —PO$_3$H$_2$, hydrogen, acetyl, isobutyryl, pivaloyl, and benzoyl, wherein each of R$_1$, R$_2$, and R$_3$ is independently selected from hydrogen and C$_{1-6}$ alkyl, and wherein n is an integer of from 1 to 10.

In an embodiment of the first aspect, the compound is of Formula (I), R$_1$ is methyl, R$_2$ is hydrogen, R$_3$ is hydrogen, and n is 3.

In an embodiment of the first aspect, the compound is of Formula (I), R$_1$ is methyl, R$_2$ is hydrogen, R$_3$ is hydrogen, and X is hydrogen.

In an embodiment of the first aspect, the compound is of Formula (I), R$_1$ is hydrogen, R$_2$ is hydrogen, R$_3$ is hydrogen, and n is 3.

In an embodiment of the first aspect, the compound is of Formula (I), R$_1$ is hydrogen, R$_2$ is hydrogen, R$_3$ is hydrogen, and X is hydrogen.

In an embodiment of the first aspect, the compound is of Formula (II), R$_1$ is methyl, R$_2$ is hydrogen, R$_3$ is hydrogen, and n is 3.

In an embodiment of the first aspect, the compound is of Formula (II), R$_1$ is hydrogen, R$_2$ is hydrogen, R$_3$ is hydrogen, and n is 3.

In an embodiment of the first aspect, the compound is administered to the individual at a daily dosage of from about 200 mg/m$^2$ to about 3000 mg/m$^2$.

In an embodiment of the first aspect, the step of administering is selected from the group consisting of orally administering, subcutaneously administering, intravenously administering, parenterally administering, and administering by inhalation.

In an embodiment of the first aspect, the method further comprises the step of administering to the individual an effective antiviral amount of an antiviral drug, for example (see the list of antiviral drugs in Appendix 2) to treat or prevent an viral infection caused by a DNA virus, a RNA virus, or a DNA or RNA reverse transcribing virus.

In a second aspect, a method of treating or preventing a human or animal viral infection caused by a DNA virus, a RNA virus, a DNA or a RNA reverse transcribing virus in an individual in need thereof is provided, comprising the step of administering to the individual an effective antiviral amount of amifostine, the free thiol form of amifostine, the disulfide of amifostine (WR-33278), a combination of both of the free thiol and the disulfide of amifostine, or other structurally and functionally related compounds as described in this document.

In a third aspect, a method of treating or preventing an infection caused by a DNA virus, a RNA virus, or a DNA or RNA reverse transcribing virus, or combination thereof in an individual in need thereof is provided, comprising the step of administering to the individual an effective antiviral amount of phosphonol, the free thiol form of phosphonol, the disulfide of phosphonol, a combination of both the free thiol and the disulfide of phosphonol, or other structurally and functionally related compounds as described in this document.

In an embodiment of the second aspect, the viral infection is caused by a dsDNA virus.

In an embodiment of the third aspect, the viral infection is caused by a dsDNA virus.

In an embodiment of the second aspect, the viral infection is caused by a dsRNA virus.

In an embodiment of the third aspect, the viral infection is caused by a dsRNA virus.

In an embodiment of the second aspect, the viral infection is caused by a (+)ssRNA virus.

In an embodiment of the third aspect, the viral infection is caused by a (+)ssRNA virus.

In an embodiment of the second aspect, the viral infection is caused by a (−)ssRNA virus.

In an embodiment of the third aspect, the viral infection is caused by a (−)ssRNA virus.

In an embodiment of the second aspect, the viral infection is caused by a non Retroviridae ssRNA reverse transcribing virus.

In an embodiment of the third aspect, the viral infection is caused by a non Retroviridae ssRNA reverse transcribing virus.

In an embodiment of the second aspect, the viral infection is caused by a dsDNA reverse transcribing virus.

In an embodiment of the third aspect, the viral infection is caused by a dsDNA reverse transcribing virus.

In an embodiment of the second aspect, the viral infection is caused by a ssDNA reverse transcribing virus.

In an embodiment of the third aspect, the viral infection is caused by a ssDNA reverse transcribing virus.

In a fourth aspect, a pharmaceutical kit is provided comprising a pharmaceutical composition comprising a compound or pharmaceutically acceptable salt or solvate thereof in a pharmaceutically acceptable carrier, the compound comprising Formula (I), Formula (II), or a combination thereof:

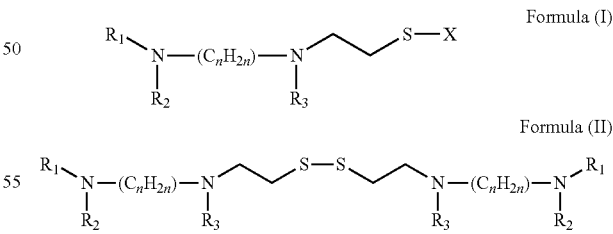

wherein X is selected from the group consisting of —PO$_3$H$_2$, hydrogen, acetyl, isobutyryl, pivaloyl, and benzoyl, wherein each of R$_1$, R$_2$, and R$_3$ is independently selected from hydrogen and C$_{1-6}$ alkyl, and wherein n is an integer of from 1 to 10; and directions for administering the pharmaceutical composition to a patient infected with a DNA virus, an RNA virus, or a DNA or RNA reverse transcribing virus.

In an embodiment of the fourth aspect, the kit further comprises an antiviral drug, selected on the basis of its effectiveness for treating the given viral agent, in a pharmaceutically acceptable carrier.

In an embodiment of the fourth aspect, the kit further comprises an antiviral drug in a pharmaceutically acceptable carrier and directions for administering the antiviral drug in a pharmaceutically acceptable carrier to the patient.

DETAILED DESCRIPTION OF THE PREFERRED EMBODIMENT

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Amifostine

Amifostine is an organic thiophosphate which selectively protects normal tissues but not tumors against cytotoxicity of ionizing radiations, DNA-binding chemotherapeutic agents (e.g., classical alkylating agents such as cyclophosphamide and non-classical alkylating agents such as mitomycin-C and platinum analogs). Amifostine is a prodrug that is dephosphorylated to the active metabolite, the free thiol form, by alkaline phosphatase and exits the bloodstream rapidly.

It has surprisingly been discovered that the compounds of preferred embodiments, including amifostine and its derivatives and analogs, are particularly effective antiviral compounds for use in inhibiting replication of diverse species of DNA viruses, RNA viruses and DNA and RNA reverse transcribing viruses.

Amifostine (referred to as "WR-2721") is marketed under the name Ethyol® by Schering-Plough Pty Ltd. It has the chemical name S-2-(3-aminopropyl)aminoethyl phosphorothioic acid and the structure:

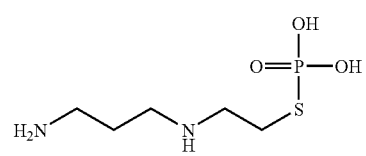 [SMILES: NCCCNCCSP(=O)(O)O]

A particularly preferred antiviral compound for use in inhibiting replication of DNA viruses, RNA viruses and DNA and RNA reverse transcribing viruses includes the free thiol form of amifostine. The free thiol form (referred to as "WR-1065") has the chemical name 2-(3-aminopropylamino)ethanethiol and the following structure:

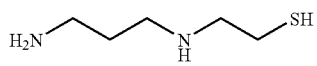

The disulfide form of amifostine (referred to as WR-33278) has the chemical name $N^1,N^3$,(dithiodiethane-2,1-diyl) dipropane-1,3-diamine

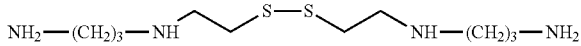

Phosphonol (referred to as "WR-3689") is structurally similar to amifostine, the only difference being the presence of a terminal methyl group. Phosphonol has the chemical name S-2-(3-(methylamino)propylamino)ethyl phosphorothioic acid and the following structure:

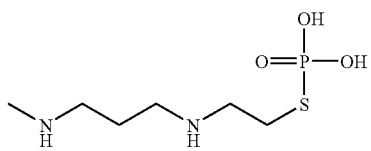

The free thiol form of phosphonol (referred to as WR-255591) has the chemical name 2-(3-(methylamino) propylamino) ethanethiol and the following structure:

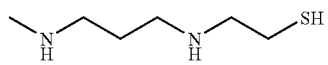

The disulfide form of phosphonol (referred to as WR-33278) has the following structure:

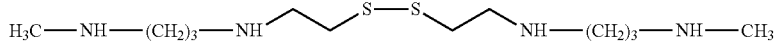

The compounds of preferred embodiments include prodrug forms of the above-described free thiol forms of amifostine, phosphonol, and analogs thereof. Such prodrugs include compounds of the structure:

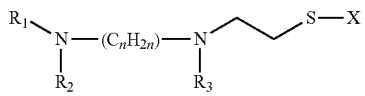

wherein each of $R_1$, $R_2$, and $R_3$ is independently selected from hydrogen and lower alkyl,
wherein —$(C_nH_{2n})$— is lower alkyl and n is 1, 2, 3, 4, 5, or (up to 10), and
wherein X is a suitable leaving group. Suitable leaving groups include —$PO_3H_2$, hydrogen, acetyl, isobutyryl, pivaloyl, and benzoyl); however, any other suitable leaving group can be employed that yields the active free thiol form of the compound when metabolized in vivo. Other leaving groups can include alkyl groups, e.g., —($C_{1-6}$ alkyl), and keto groups, e.g., —C(=O)—($C_{1-6}$ alkyl) or —C(=O)—($C_{6-18}$ aryl).

The term "lower alkyl" as used herein is a broad term, and is to be given its ordinary and customary meaning to a person of ordinary skill in the art (and is not to be limited to a special or customized meaning), and refers without limitation to a straight chain or branched chain, acyclic or cyclic, saturated aliphatic hydrocarbon containing 1, 2, 3, 4, 5, or 6 carbon atoms. Saturated straight chain lower alkyls include methyl, ethyl, n-propyl, n-butyl, n-pentyl, and n-hexyl; while representative saturated branched chain alkyls include isopropyl, sec-butyl, isobutyl, tert-butyl, and isopentyl. "aryl," as used herein is a broad term and is used in its ordinary sense, including, without limitation, to refer to an aromatic carbocyclic moiety such as phenyl or naphthyl, including mono-, di-, and poly-homocyclic aromatic ring systems (e.g., $C_{6-18}$ aryl).

The prodrug forms described above are metabolized into active thiols of the formula:

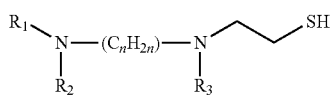

wherein each of $R_1$, $R_2$, $R_3$, —($C_nH_{2n}$)—, and n is as defined above. In a particularly preferred embodiment, —($C_nH_{2n}$)— is a straight alkyl chain having three carbon atoms. It is also particularly preferred that $R_2$ and $R_3$ are both hydrogen, and that $R_1$ is hydrogen or methyl.

In addition to the thiols, certain disulfide forms also exhibit antiviral activity, for example, a disulfide of the following structure:

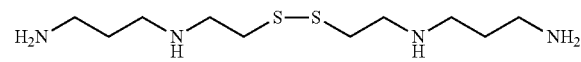 [SMILES: NCCCNCCSSCCNCCCN]

can also be employed as an antiviral agent.

Other antiviral agents of preferred embodiments incorporate a cysteamine-like group (i.e., a group containing the moiety >N—($CH_2$)$_2$—S—), or a moiety with the structure of WR 2721 or WR-1065, tethered to a DNA or nucleic acid binding agent, or other agents with some affinity for nucleic acids or proteins.

The compounds of preferred embodiments are particularly effective antiviral agents for monotherapeutic or combined-therapeutic use in treating DNA viruses, RNA viruses and DNA and RNA reverse transcribing viruses. The compounds of preferred embodiments are generally administered at dosages equal to or less than the oral radioprotective dosage of amifostine (e.g., 1456 mg total dose, or 910 mg/m² for a 60 kg body weight (BW) adult human) or phosphonol (e.g., 725 mg/m²). In adults undergoing chemotherapy, the recommended starting dose of amifostine is 910 mg/m² for a 60 kg BW adult human administered once daily as a 15-minute i.v. infusion, starting 30 minutes prior to chemotherapy. Similar dosing regimens can be employed for use of the compounds of preferred embodiments when used as antiviral agents. Dosages can be converted from mg/m² to total mg or mg/kg BW (see, e.g., Freireich et al. (1966), Cancer Chemother. Reports, 50 (4) 219-244) as in Table 2.

TABLE 2

| Species | Body Wt. (Kg) | Body Surface area (m²) | Km factor |
| --- | --- | --- | --- |
| Mouse | 0.2 | 0.0066 | 3.0 |
| Rat | 0.15 | 0.025 | 5.9 |
| Monkey | 3.0 | 0.24 | 12 |
| Dog | 8.0 | 0.40 | 20 |
| Human child | 20.0 | 0.80 | 25 |
| Human adult | 60.0 | 1.60 | 37 |

It is generally preferred to administer amifostine (or other compounds of preferred embodiments) at dosages of 910 mg/m² or less. This dosage is equivalent to 24.3 mg/kg BW for a 60 kg BW adult human being (or a total dose of 1456 mg for a 60 kg BW adult, as described above); however, in certain embodiments it can be desirable to administer the compounds of preferred embodiments at higher dosage levels. For example, children have been given up to a 2700 mg/m² total dose of amifostine prior to administration of a chemotherapeutic agent. In some individuals such high doses are associated with side effects. A dose of 740 mg/m² amifostine (1148 mg total, for a 60 kg BW human adult) is associated with fewer side effects (List et al. (1997), Blood 90(9): 3364-9), and is thus generally preferred. For daily dosing, 200-340 mg/m² of amifostine (544 mg total dose for a 60 kg BW adult) is generally preferred (Schuchter (1996), Semin Oncol 23(4 Suppl 8): 40-3; Santini et al. (1999), Haematologica 84(11): 1035-42).

Rodent studies suggest the use of higher dosages. For example, the maximally tolerated dose (MTD) for WR-2721 in mice was 432 mg/kg (BW) administered i.p. and 720 mg/kg BW administered p.o., and the 100% effective radioprotective dose was about one half of the MTD. For phosphonol, the MTD was 893 mg/kg BW administered i.p. and 1488 mg/kg BW administered p.o., and the 100% effective radioprotective dose was about one half of the MTD. All of the aminothiols have MTDs in rodents of greater than 400 mg/kg BW.

Amifostine and WR-1065 can be efficacious at very low concentrations, for example, down to 0.4 micromolar concentrations in some in vitro studies. In a preferred embodiment, a drug delivery system that obtains relatively constant intracellular concentrations over a period of time that could extend from several days to up to one year or more is desired. To achieve this goal, we anticipate using drug delivery systems demonstrated to achieve relatively constant intracellular drug levels over extended time periods. Examples of such drug delivery systems include subcutaneous administration, formulation in nanoparticles, were formulation in other slow release systems.

Table 3 provides plasma concentrations of amifostine metabolites (see Geary et al., Res. Comm. Chem. Path. Pharmacol., 65(2), 147-159 (1989)) and phosphonol metabolites (see Buckpitt et al., Contract #DAMD 17-86-C-6177, reference obtained from Dr. D. Grdina, personal communication) after duodenal administration of 150 mg/kg BW of each drug in rhesus macaques. This data was collected as part of work performed to evaluate the radioprotective activity of the compounds. These data may be useful in estimating plasma concentrations in humans.

TABLE 3

| Drug | Time after Administration (h) | Concentration (µg/ml) |
| --- | --- | --- |
| WR-1065[1] | 1 | 6.21 |
| WR-1065[1] | 2 | 4.14 |
| WR-1065[1] | 6 | 2.07 |
| Phosphonol[2] | 1 | 11.75 |
| Phosphonol[2] | 2 | 17.08 |
| Phosphonol[2] | 6 | 15.50 |

Note:
40 µM WR-1065 = 8.28 µg/ml

While it is generally preferred to formulate amifostine or the other compounds of preferred embodiments for oral administration, the compounds of preferred embodiments can be formulated so as to allow them to be administered by other routes, as discussed herein. It can be desirable in certain embodiments to formulate amifostine for intravenous administration in order to maximize efficacy. Because of the structural similarities between amifostine and phosphonol, especially the similarities in the sulfhydryl ends of the molecules, phosphonol is expected to behave in a manner similar to amifostine rather than WR-151327 (chemical formula $CH_3NH(CH_2)_3NH(CH_2)_3SPO_3H_2$). WR-151327 has been previously shown to have anti-HIV activity; this activity was attributed to the ability of the compound to modulate cytokine levels in a manner that inhibited HIV replication and/or proliferation (Kalebic et al., 1994).

Phosphonol may not be quite as efficacious as amifostine, based upon the work of Gutschow et al., who found lower activity when a methyl group was substituted for a hydrogen atom in a position similar to that of the methyl group of phosphonol that distinguishes its structure from that of amifostine (Gutschow et al. (1995), *Pharmazie* 50(10): 672-5). However, phosphonol is expected to be significantly more efficacious than WR-151327. This consideration should be viewed in light of the fact that the overall structures of the compounds tested by Gutschow et al. were significantly different from the structures of the preferred embodiments. The overall structures of the compounds tested by Gutschow et al. are significantly different from the structures of the preferred embodiments, and it is expected that phosphonol will be significantly more efficacious than WR-151327.

Amifostine, its analogs, and its derivatives can be administered in combination with other antiviral agents employed to treat HIV infection. One of the benefits of such combination therapies is that lower doses of the other antiviral agents can be administered while still achieving a similar level of antiviral efficacy. Such lower dosages can be particularly advantageous for drugs known to have genotoxicity and mitochondrial toxicity (for example, some nucleoside analogs). Conversely, greater efficacy might be achieved using therapeutic doses of two drugs than could be achieved using only a single drug.

The most common antiviral drugs that can be used in junction with the compounds of preferred embodiments include, but are not limited to, members of the class of drugs known as nucleoside analogs. Other agents that could be used potentially are included in the list of antiviral drugs included in Appendix 2. The use of nucleoside analogs has been associated with a variety of side effects due to the fact that these drugs are analogs of naturally occurring nucleosides, are incorporated into host cell DNA, and function as obligate DNA chain terminators. As such, these drugs are associated with the induction of mutations in host cell DNA, increased risks for certain types of cancer, as well as increased risks for a variety of diseases associated with mutation induction in nuclear and mitochondrial DNA. Nucleoside analogs are also associated with mitochondrial toxicity to a degree that varies depending upon the specific nucleoside analog in question. Thus, it is desirable to be able to minimize the doses of nucleoside analogs used, and/or to use these drugs in combination with other drugs with demonstrated antiviral efficacy that does not compromise the effectiveness of the other treatment, and that also has demonstrated antimutagenic efficacy.

The use of the compounds of preferred embodiments have been tested in cell culture with one nucleoside analog (zidovudine), and it is been demonstrated that the efficacy of each compound is not diminished when used in combination with the other. It is anticipated that the compounds of preferred embodiments can also be effectively employed with other nucleoside analogs and with other antiviral agents (see Appendix 2).

Pharmaceutical Compositions Comprising Amifostine and Analogs Thereof:

The compounds of preferred embodiments (including derivatives, isomers, metabolites, prodrugs, or pharmaceutically acceptable esters, salts, and solvates thereof) can be incorporated into a pharmaceutically acceptable carrier, including incorporation into nanoparticles for administration to an individual having a viral infection (for example, an adenoviral infection as an example of a DNA virus, an influenza infection as an example of a RNA virus, or an HIV infection as an example of a DNA or RNA reverse transcribing virus) or can be administered prophylactically to prevent viral infection, or postinfection to decrease symptoms upon viral infection. The compounds of preferred embodiments can be employed as the sole agent in the prevention or treatment of DNA viruses, RNA viruses, or DNA or RNA reverse transcribing viruses, and/or combinations thereof two or more such compounds can be employed, optionally in combination with other therapeutic agents, e.g., conventional or newly developed drugs employed in the treatment of AIDS or HIV, or other viral infections.

Because certain of the compounds of preferred embodiments can be sensitive to oxidation, it can be desirable to administer the compounds in combination with reducing agents including, but not limited to, vitamin C and vitamin E. Other reducing agents include organic aldehydes, hydroxyl-containing aldehydes, and reducing sugars such as glucose, mannose, galactose, xylose, ribose, and arabinose. Other reducing sugars containing hemiacetal or keto groupings can be employed, for example, maltose, sucrose, lactose, fructose, and sorbose. Other reducing agents include alcohols, preferably polyhydric alcohols, such as glycerol, sorbitol, glycols, especially ethylene glycol and propylene glycol, and polyglycols such as polyethylene and polypropylene glycols.

The terms "pharmaceutically acceptable salts" and "a pharmaceutically acceptable salt thereof" as used herein are broad terms, and are to be given their ordinary and customary meaning to a person of ordinary skill in the art (and are not to be limited to a special or customized meaning), and refer without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity. In addition to salts, pharmaceutically acceptable precursors and derivatives of the compounds can be employed. Pharmaceutically acceptable amides, lower alkyl esters, and protected derivatives can also be suitable for use in compositions and methods of preferred embodiments. While it may be possible to administer the compounds of the preferred embodiments in the form of pharmaceutically acceptable salts, it is generally preferred to administer the compounds in neutral form.

It is generally preferred to administer the compounds of preferred embodiments orally; however, other routes of administration are contemplated. Contemplated routes of administration include but are not limited to oral, sublingual, parenteral, transcutaneous, subcutaneous, intravenous, and by inhalation. Compounds of preferred embodiments can be formulated into liquid preparations for, e.g., oral administration. Suitable forms for such administration include suspensions, syrups, and elixirs.

The pharmaceutical compositions of preferred embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In certain embodiments it can be desirable to maintain the active compound in the reduced state. Accordingly, it can be desirable to include a reducing agent, such as vitamin C, vitamin E, or other reducing agents as are known in the pharmaceutical arts, in the formulation.

Viscosity of the pharmaceutical compositions can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents.

A pharmaceutically acceptable preservative can be employed to increase the shelf life of the pharmaceutical compositions. Benzyl alcohol can be suitable, although a variety of preservatives including, for example, parabens, thimerosal, chlorobutanol, or benzalkonium chloride can also be employed. A suitable concentration of the preservative is typically from about 0.02% to about 2% based on the total weight of the composition, although larger or smaller amounts can be desirable depending upon the agent selected. Reducing agents, as described above, can be advantageously used to maintain good shelf life of the formulation.

The compounds of preferred embodiments can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, colors, and the like, depending upon the route of administration and the preparation desired. See Standard texts, such as "*Remington: The Science and Practice of Pharmacy*", Lippincott Williams & Wilkins; 20th edition (Jun. 1, 2003) and "*Remington's Pharmaceutical Sciences*," Mack Pub. Co.; 18th and 19th editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the active ingredient in admixture with excipients suitable for the manufacture of aqueous suspensions.

Formulations for oral use can also be provided as hard gelatin capsules, wherein the active ingredient(s) are mixed with an inert solid diluent, such as calcium carbonate, calcium phosphate, or kaolin, or as soft gelatin capsules. In soft capsules, the active compounds can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers. In instances where it is desirable to maintain a compound of a preferred embodiment in a reduced form (in the case of certain active metabolites), it can be desirable to include a reducing agent in the capsule.

Tablets can be uncoated or coated by known methods to delay disintegration and absorption in the gastrointestinal tract and thereby provide a sustained action over a longer period of time. For example, a time delay material such as glyceryl monostearate can be used. When administered in solid form, such as tablet form, the solid form typically comprises from about 0.001 wt. % or less to about 50 wt. % or more of active ingredient(s), preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets can contain the active ingredients in admixture with non-toxic pharmaceutically acceptable excipients including inert materials. For example, a tablet can be prepared by compression or molding, optionally, with one or more additional ingredients. Compressed tablets can be prepared by compressing in a suitable machine the active ingredients in a free-flowing form such as powder or granules, optionally mixed with a binder, lubricant, inert diluent, surface active or dispersing agent. Molded tablets can be made by molding, in a suitable machine, a mixture of the powdered compound moistened with an inert liquid diluent.

Preferably, each tablet or capsule contains from about 10 mg or less to about 1,000 mg or more of a compound of the preferred embodiments, more preferably from about 20, 30, 40, 50, 60, 70, 80, 90, or 100 mg to about 150, 200, 250, 300, 350, 400, 450, 500, 550, 600, 650, 700, 750, 800, or 900 mg. Most preferably, tablets or capsules are provided in a range of dosages to permit divided dosages to be administered. A dosage appropriate to the patient and the number of doses to be administered daily can thus be conveniently selected. In certain embodiments it can be preferred to incorporate two or more of the therapeutic agents to be administered into a single tablet or other dosage form (e.g., in a combination therapy); however, in other embodiments it can be preferred to provide the therapeutic agents in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Surfactants can also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations can be employed wherein the amifostine or analog(s) thereof is incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments can be added for identification or to characterize different combinations of active compound doses.

When administered orally in liquid form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

When a compound of the preferred embodiments is administered by intravenous, parenteral, or other injection, it is preferably in the form of a pyrogen-free, parenterally acceptable aqueous solution or oleaginous suspension. Suspensions can be formulated according to methods well known in the art using suitable dispersing or wetting agents and suspending agents. The preparation of acceptable aqueous solutions with suitable pH, isotonicity, stability, and the like, is within the skill in the art. A preferred pharmaceutical composition for injection preferably contains an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils can be employed conventionally as a solvent or suspending medium. For this purpose, any bland fixed oil can be employed including synthetic mono or diglycerides. In addition, fatty acids such as oleic acid can likewise be used in the formation of injectable preparations. The pharmaceutical compositions can also contain stabilizers, preservatives, buffers, antioxidants, or other additives known to those of skill in the art.

The duration of the injection can be adjusted depending upon various factors, and can comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

The antiviral compositions of the preferred embodiments can additionally employ adjunct components conventionally found in pharmaceutical compositions in their art-established fashion and at their art-established levels. Thus, for example, the compositions can contain additional compatible pharmaceutically active materials for combination therapy (such as supplementary antimicrobials, antipruritics, astringents, local anesthetics, anti-inflammatory agents, reducing agents, and the like), or can contain materials useful in physically formulating various dosage forms of the preferred embodiments, such as excipients, dyes, thickening agents, stabilizers, preservatives or antioxidants.

The compounds of the preferred embodiments can be provided to an administering physician or other health care professional in the form of a kit. The kit is a package which houses a container which contains the compound(s) in a suitable pharmaceutical composition, and instructions for administering the pharmaceutical composition to a subject. The kit can optionally also contain one or more additional therapeutic agents, e.g., antiviral nucleoside analog, peptide analog, protease inhibitor, monoclonal antibody, or any other antiviral used for the treatment or prevention of virus disease (see for example Appendix 2). For example, a kit containing one or more compositions comprising compound(s) of the preferred embodiments in combination with one or more additional antiviral, antibacterial, and/or anti-infective agents can be provided, or separate pharmaceutical compositions containing a compound of the preferred embodiments and additional therapeutic agents can be provided. The kit can also contain separate doses of a compound of the preferred embodiments for serial or sequential administration. The kit can optionally contain one or more diagnostic tools and instructions for use. The kit can contain suitable delivery devices, e.g., syringes, and the like, along with instructions for administering the compound(s) and any other therapeutic agent. The kit can optionally contain instructions for storage, reconstitution (if applicable), and administration of any or all therapeutic agents included. The kits can include a plurality of containers reflecting the number of administrations to be given to a subject. In a particularly preferred embodiment, a kit for the treatment of DNA viruses, RNA viruses, and DNA and RNA reverse transcribing viruses, and combinations thereof is provided that includes amifostine or another compound of a preferred embodiment and one or more antiviral agents currently employed to treat the virus. Antiviral agents include for example, nucleoside analogs such as acyclovir, reverse transcriptase inhibitors such as zidovudine, didanosine, zalcitabine, stavudine, 3TC; non-nucleoside reverse transcriptase inhibitors; protease inhibitors; cytokines; immunomodulators, and antibodies but are not limited thereto.

The compounds of the preferred embodiments can be administered prophylactically for the prevention of DNA virus, RNA virus, or DNA or RNA reverse transcribing virus infection. Alternatively, therapy is preferably initiated as early as possible following the onset of signs and symptoms of a viral infection, or following exposure to a DNA virus, a RNA virus, or a DNA or RNA reverse transcribing virus infection. The administration route, amount administered, and frequency of administration will vary depending on the age of the patient, the severity of the infection, and any associated conditions. Contemplated amounts, dosages, and routes of administration for the compounds of preferred embodiments for treatment of a DNA virus, a RNA virus, or a DNA or RNA reverse transcribing virus infection are similar to those established for conventional antiviral agents. Detailed information relating to administration and dosages of conventional antiviral agents can be found in the Physician's Desk Reference, 47th edition. This information can be adapted in designing treatment regimes utilizing the compounds of preferred embodiments. It is expected that antiviral therapies combining an aminothiol with another antiviral therapy will have an additive or synergistic activity, making it possible to reduce the doses of the drugs currently used to treat DNA virus, RNA virus, or DNA or RNA reverse transcribing virus infection, or making it possible to achieve higher efficacy by using therapeutic doses of two or more agents together. The combination of an aminothiol with a nucleoside analog is expected to simultaneously provide improved antiviral therapy and protection against nucleoside analog-induced side effects, especially those associated with nuclear DNA or mitochondrial DNA damage. It is further anticipated that an aminothiol could protect against deleterious side effects of another antiviral drugs, especially those that induce nuclear DNA or mitochondrial DNA damage.

According to one embodiment, contemplated amounts of the compounds of the preferred embodiments for oral administration to treat DNA virus, RNA virus, or DNA or RNA reverse transcribing virus infection are from about 10 mg or less to about 2000 mg or more administered from about every 4 hours or less to about every 6 hours or more (or from about 4 times daily to about 6 times daily) for about 5 days or less to about 10 days or more (40 mg/day or less to about 15,000 mg/day or more) or until there is a significant improvement in the condition. For suppressive therapy to inhibit the onset of infection in susceptible individuals, doses of from about 10 mg or less to about 1000 mg or more are orally administered once, twice, or multiple times a day, typically for up to about 12 months, or, in certain circumstances, indefinitely (from about 10 mg/day to about 1,000 mg/day). When treatment is long term, it can be desirable to vary the dosage, employing a higher dosage early in the treatment, and a lower dosage later in the treatment.

The single highest dose of amifostine administered to an adult human as documented in the literature was 1330 mg/m$^2$. Children have been administered single doses of amifostine of up to 2700 mg/m$^2$ with no untoward effects. The literature indicates that multiple doses (up to three times the recommended single dose of 740 to 910 mg/m$^2$) have been safely administered within a 24-hour period. Repeated administration of amifostine at two and four hours after the initial dose does not appear to result in an increase in side effects, especially nausea, vomiting, or hypotension. It appears that the most significant deleterious side effect from the administration of amifostine is hypotension.

According to one embodiment, contemplated amounts of the compounds of the preferred embodiments, methods of administration, and treatment schedules for individuals with infections caused by DNA viruses, RNA viruses and DNA and RNA reverse transcribing viruses are generally similar to those described above for the prevention of and/or treatment of radiation- or chemotherapy-induced cytotoxicity; they may also be similar to those used for the treatment of myelodysplastic syndrome.

Known side effects of amifostine include decrease in systolic blood pressure, nausea, and vomiting. If such side effects are observed for the particular thiophosphate administered, it is generally preferred to administer an antiemetic medication prior to, or in conjunction with the thiophosphate. Suitable antiemetic medications include antihistamines (e.g., buclizine, cyclizine, dimenhydrinate, diphenhydramine, meclizine), anticholinergic agents (e.g., scopolamine), dopamine antagonists (e.g., chlorpromazine, droperidol, metoclopramide, prochlorperazine, promethazine), serotonin antagonists (e.g., dolasetron, granisetron, ondansetron), or other agents (e.g., dexamethasone, methylprednisolone, trimethobenzamide).

The purity of the WR-1065 used in the experiments described below is unknown. WR-1065 is sensitive to oxidation (and possibly other reactions) and can undergo reaction to forms that appear to lack antiviral activity. Accordingly, in the tables below and in the preferred dosages provided above, the indicated concentrations represent the maximum amount of active compound that could be present; the true concentration of active compound is less than that indicated but cannot be determined definitively. In addition, for concentrations of WR-1065 of less than 100 µM, estimates of the true efficacy of the compound are limited by the fact that the compound has been found to be inactivated by a variety of medium components (Grdina et al. (2000), *Drug Metabol Drug Interact* 16(4): 237-79.). Below approximately 50 µM, this problem becomes especially severe.

The impact of WR1065 treatment on replication on lung prototypic adenovirus strains in A549 cell monolayers is illustrated in Table 4. A549 or MDCK cells were used for the plaque reduction assays. Cells were grown to near confluence in Minimal Essential Medium (MEM) in six-well plates. Cells were infected with 100 plaque forming units (PFUs) of virus of virus in 100 µl and adsorption was allowed for one hour at 37° C. Cell monolayers were subsequently overlaid with 0.6% agarose in MEM. The overlay medium was prepared to contain a final concentration of 10 µM, 33 µM and 100 µM amount of WR 1065. Each concentration was assayed in triplicate. Wells overlaid with media without WR-1065 were set up as 100% infectious virus yield controls. Cultures were maintained at 37° C. in 5% $CO_2$ for 7 days. At the end of this time period, cell cultures were fixed with 1% formaldehyde and stained with Crystal Violet for visualization of plaques and evaluation of plaque size and number. Reduction of plaque formation was expressed as a percentage of the untreated controls. Subsequently, WR 1065 was demonstrated to inhibit viral replication and development of cytotopathic effect in a dose-dependent manner in influenza A or influenza B-infected MDCK cell monolayers. Using an approach similar to that described above, MDCK cells growing in 6-well plates were infected with 100 plaque forming units (PFUs) of virus in 100 µl and adsorption was allowed for one hour at 37° C. Cell monolayers were subsequently overlaid with 0.6% agarose in MEM. The overlay medium was prepared to contain a final concentration of 10 µM, 33 µM and 100 µM amount of WR 1065. Each concentration was assayed in triplicate. Wells overlaid with media without WR-1065 were set up as 100% infectious virus yield controls. Cultures were maintained at 37° C. in 5% $CO_2$ for 3 days. At the end of this time period, cell cultures were fixed with 1% formaldehyde and stained with Crystal Violet for visualization of plaques and evaluation of plaque size and number. Reduction of plaque formation was expressed as a percentage of the untreated controls.

TABLE 4

| | | | | Mean infectious virus yields (PFUs ×10$^6$) 96-h post infection & WR 1065 treatment[a] | | | |
|---|---|---|---|---|---|---|---|
| Virus | Species | Susceptible populations | Trial # | 0 µM WR 1065 | <10 µM WR 1065 | <33 µM WR 1065 | <100 µM WR 1065 |
| Ad7-p (strain Gomen) | B | Pediatric & military; respiratory infection | 1 | 3.5 | 1.85 | 0.85 | 1.15 |
| | | | 2 | 58.2 | — | — | 30.5 |
| Ad5-p (strain Adenoid 75) | C | Immuno-compromised; upper respiratory | 1 | 12.5 | 9.0 | 5.65 | 2.25 |
| | | | 2 | 665 | — | 600 | 500 |
| | | | 3 | 1,920 | — | 1,660 | — |
| Ad4-p (strain RI-67) | E | Military; conjunctivitis & respiratory infection | 1 | 1,900 | — | 1,420 | 980 |
| | | | 2 | 22.5 | — | — | 9.5 |

Table 5 includes data from an experiment to measure WR-1065 protection against cytopathic effects in MDCK cell monolayers infected with influenza A/Puerto Rico/8/34 (H1N1), using densitometry readings of the stained cell monolayers to estimate relative cell survival. Similar results were obtained in a second independent experiment using influenza A/Puerto Rico/8/34 (H1N1), and in an experiment using the same approach with influenza B/Lee/40. In a third experiment with influenza A, WR 1065 was added to an agarose overlay following a one-hour adsorption with a different virus strain, A/HKx31 (H3N2), and a plaque reduction assay was performed (Table 5). The results illustrate protection of MDCK cells from Influenza A by WR 1065, based upon densitometry readings (experiment 1) or a plaque reduction assay (experiment 2)

According to one aspect of the present invention, the reduced form of amifostine (WR 2721 or ethyol), was the most active moiety in the observed antiviral effects. In another aspect of the present invention, WR-1065, was the most active moiety in the observed antiviral effects. A common medium component (phenylalanine) blocks the activity of WR 1065 to some undetermined degree.

TABLE 5

| Influenza A strain; | Amount of WR 1065[a] | | | |
|---|---|---|---|---|
| Quantitative approach | 0 µM | <10 µM | <33 µM | <100 µM |
| Experiment 1 | | | | |
| A/Puerto Rico/8/34(H1N1); Densitometry reading[b] | 9.57 ± 0.3 × 10$^5$ | 12.4 ± 0.4 × 10$^5$ | 13.1 ± 1.0 × 10$^5$ | 14.3 ± 1.5 × 10$^5$ |

TABLE 5-continued

| Influenza A strain; | Amount of WR 1065[a] | | | |
|---|---|---|---|---|
| Quantitative approach | 0 µM | <10 µM | <33 µM | <100 µM |
| Experiment 2 | | | | |
| A/HKx31(H3N2); Mean plaque number | 66.3 | 59.3 | 57 | 48 |

Densitometry readings=mean counts/mm$^2$±standard deviation using Quantity One (Bio-Rad) plate reader.

Protection of A549 cells from the cytopathic effects of Adenovirus 5p by WR-1065 as assessed by a plaque reduction assay is illustrated in Table 6.

TABLE 6

| | Amount of WR1065 | | |
|---|---|---|---|
| | 0 µM | 16.5 µM | 50 µM |
| Adenovirus 5p | 64 | 63 | 41 (36% reduction) |

Experiments were conducted to determine the antiretroviral effects of AZT in the presence of WR-1065, the active metabolite of amifostine. Peripheral blood mononuclear cells (PBMCs) obtained from the NIH Blood Bank were cultured with phytohemagglutinin (PHA) for 48 hours to create PHA blasts. The cells were cultured in RPMI-1640 medium with 10% fetal bovine serum (FBS), 1% penicillin/streptomycin and glutamine, and 10% Interleukin-2 (IL-2). The PHA blasts were then infected with HIV for two hours (see Perno et al. (1988), *J. Exptl. Med.* 168:111; Aquaro et al. (1988), *J. Medical Virology* 68:479-488).

Noting the caveats outlined above regarding purity of the WR-1065 used, WR-1065 (from the NCI Chemical Carcinogen Repository; see Hoffman et al. (2001), *Env. Mol. Mut.* 37:117) was weighed (Mol. Wt. 134) and stored frozen in RPMI-1640 medium as a 10 mg/ml solution (13.4 µL of the solution added to 1 ml of RPMI-1640 yields 1000 µM solution). AZT (SIGMA, Mol. Wt. 267) was dissolved in phosphate-buffered saline (PBS) at a concentration of 36 mM (9.72 mg/ml), 0.01 ml (97 µg) of the resulting solution was added to 3.6 ml RPMI-1640 medium to yield a 26.9 µg/ml solution, and 0.1 ml (2.69 µg) of that resulting solution was added to 1 ml of RPMI-1640 medium to yield a 10 µM solution of AZT. The HIV-infected PHA blasts were incubated with 10 µM AZT in the presence or absence of 1000 µM WR-1065 prepared as described above.

At 72 hours, HIV infection status was monitored in five experimental groups by measuring p24 using an ELISA kit (RETRO-TEK HIV-1, p24 Extended Range ELISA, ZMC catalog #0801137). The HIV infection status for the five experimental groups is provided in Table 3 (see Experiment #1 data).

TABLE 7

| Treatment Group | 10 µM AZT | WR1065 | HIV P24 pg/ml | Estimated percent viral inhibition |
|---|---|---|---|---|
| Experiment #1 | | | | |
| PHA blasts | No | No | 0.28 | N.A. |
| PHA blasts + HIV | No | No | 498.62 | N.A. |

TABLE 7-continued

| Treatment Group | 10 µM AZT | WR1065 | HIV P24 pg/ml | Estimated percent viral inhibition |
|---|---|---|---|---|
| PHA blasts + HIV | Yes | No | 0.13 | ~100% |
| PHA blasts + HIV | Yes | Yes (1000 µM) | 0.13 | ~100% |
| PHA blasts + HIV | No | Yes (1000 µM) | 0.13 | ~100% |
| Experiment #2 | | | | |
| PHA blasts | No | No | 8.99 | N.A. |
| PHA blasts + HIV | No | No | 176.45 | N.A. |
| PHA blasts + HIV | Yes | No | 9.07 | 94.9% |
| PHA blasts + HIV | No | Yes (1000 µM) | 8.92 | 94.9% |
| PHA blasts + HIV | No | Yes (330 µM) | 9.31 | 94.7% |
| PHA blasts + HIV | No | Yes (100 µM) | 8.92 | 94.9% |
| Experiment #3 | | | | |
| PHA blasts | No | No | 3.0 | N.A. |
| PHA blasts + HIV | No | No | 44,455.8 | N.A. |
| PHA blasts + HIV | Yes | No | 2.9 | ~100% |
| PHA blasts + HIV | No | Yes (66 µM) | 33.2 | 99.9% |
| PHA blasts + HIV | No | Yes (33 µM) | 503.2 | 98.9% |
| PHA blasts + HIV | No | Yes (10 µM) | 911.2 | 98.0% |
| PHA blasts + HIV | No | Yes (5 µM) | 10,293.7 | 76.8% |

Table 7 illustrates the antiviral efficacy of AZT and WR-1065 on PHA blasts. Subsequent experiments confirmed this antiretroviral effect, and demonstrated that the ability of WR 1065 to inhibit viral replication was dose-dependent and comparable in concentration and effect to that seen with AZT alone using this in vitro assay system.

The results of these experiments illustrate that WR-1065 and some structurally-related aminothiols function as broad-spectrum antiviral agents. Taken together, these results further support the hypothesis that the antiviral activity of WR-1065 is due to its ability to bind to specific sites on viral RNA, because the only known element common to the tested viruses is their requirement for the formation and use of RNA during viral replication (Table 7).

Viability of Human Cells in the Presence of WR-1065

Experiments were conducted to determine the viability of cells exposed to various concentrations of WR-1065. Tests were conducted on PHA blasts cultured as described for the previous experiments, but were not incubated in the presence of HIV. WR-1065 was prepared from a 10 mg/ml solution in RPMI-1640 medium and diluted to the desired concentrations. Cell viability was measured 72 hours after exposure to WR-1065. Percentage of viable cells (compared to unexposed controls) is provided in Table 8.)

TABLE 8

| WR-1065 Concentration (µM) | % Viable Cells (compared to control) |
|---|---|
| 1000 | 30 |
| 500 | 73 |
| 100 | 63 |
| 50 | 89 |

TABLE 8-continued

| WR-1065 Concentration ($\mu$M) | % Viable Cells (compared to control) |
|---|---|
| 10 | 90 |
| 5 | 82 |
| 1 | 83 |

The test results demonstrated acceptable cell viability for all concentrations tested, and particularly good cell viability for concentrations of 50 µM and lower.

Comparison of Anti-Viral Activity of Cysteamine and WR-1065

Cysteamine (chemical formula $H_2NCH_2CH_2SH$) has been demonstrated to have anti-HIV activity (Ho et al. (1995), *AIDS Res Hum* Retroviruses 11(4): 451-9; Bergamini et al. (1996), *J Infect Dis* 174(1): 214-8). Using an in vitro assay system as described above, 200 µM cysteamine effectively suppressed (~100%) HIV replication. In comparison, WR-1065 effectively suppressed (>99.9%) HIV replication at a concentration of less than 100 µM. Thus, the in vitro anti-HIV activity of WR-1065 is over 2-fold higher than that of cysteamine. In addition, cysteamine's duration of action was determined to be very short; to achieve an anti-HIV effect, fresh cysteamine had to be added to the cell culture system every 12 hours. WR-1065, however, had a long duration of action—it only had to be added to the culture system once in a 72 hour period.

Comparison of Anti-Viral Activity of Cystamine and WR-1065

Cystamine (chemical formula $H_2N(CH_2)_2SS(CH_2)_2NH_2$), the oxidized form of cysteamine, has been demonstrated to have anti-HIV activity, DNA binding capacity, radioprotective capacity, and the ability to shift the equilibrium of DNA from the A-form towards the B-form (Allegra et al. (2002), *Amino Acids* 22(2): 155-66). WR-1065, the active form of WR-2721, has also been shown to bind to DNA in the minor groove, and also to shift the B/A-DNA equilibrium towards the B-form. Accordingly, it can be inferred that cystamine and its reduced form cysteamine are capable of binding to other nucleic acids in addition to DNA, and have some ability to bind to and/or to interact with proteins. It should be noted that the anti-HIV activity of cystamine is considered to be due, at least in large part, to its rapid in vivo conversion to cysteamine.

A comparison of the DNA phosphate binding capacity of cystamine versus WR-1065 demonstrated that these two compounds have similar binding affinities under similar in vitro conditions (Smoluk et al. (1986), *Radiat Res.* 107(2): 194-204). However, WR-1065 is a larger molecule than cysteamine because it contains an additional moiety: —$(CH_2)_3NH_2$. Thus, it can be hypothesized that WR-1065 can bind to and thereby block a larger fragment of a nucleic acid than cysteamine. It can therefore be hypothesized that the differential binding characteristic of WR-1065 versus cysteamine may be responsible for WR-1065's improved antiviral efficacy. It is possible that WR-1065's antiviral activity is due in part to its ability to bind to and to block critical sites on nucleic acids and/or proteins. (Allegra et al. (2002), *Amino Acids* 22(2): 155-66; North et al., (2002), *Mol. Carcinog.* 33(3): 181-8). Blockage of nucleic acid sites and/or proteins is considered to be a possible mechanism for the aminothiols' modulation of enzyme function (Brekken et al. (1986), *J Biol Chem* 273(41): 26317-22). The mechanism by which an aminothiol could bind to and/or block nucleic acids and/or proteins without inducing significant cytotoxicity to eukaryotic cells is unknown at this time.

As further evidence of the potential importance of WR-1065's nucleic acid binding capacity to its antiviral activity, it has been demonstrated that WR-1065 has antiviral efficacy against three different species of adenovirus and two different strains of influenza. These are dramatically different types of viruses with significantly different modes of replication. One common replication element shared by all of these viruses, as well as HIV, is a requirement for single or double-stranded RNA during part of the replication cycle. Thus, the demonstration of broad-spectrum antiviral activity supports the hypothesis that the ability of the antiviral agent WR-1065 to bind to RNA plays a role in the observed antiviral effect.

Discussion

While not wishing to be bound by any particular theory, it is believed that one or more of the compounds of the present invention function as an antiviral agent because its structure renders it bi-functional, combining two distinct properties. For example, the —$(CH_2)_3NH_2$ portion of WR-1065 is believed to be responsible for binding to nucleic acids (DNA, RNA), and possibly also to some proteins. A second portion of WR-1065 —$NH(CH_2)_2SH$ is believed to be largely responsible for the antiretroviral/antiviral effects that have been observed to be effective against some viruses, it is believed that the sulfhydryl group needs to be in the reduced state in order for antiretroviral/antiviral effects to be observed for the compound; however, it is possible that the sulfhydryl group may remain functional if oxidized to the disulfide (as in WR-33278). Both of these components contribute to maximizing antiretroviral/antiviral effects of the compounds of preferred embodiments (e.g., both the —$(CH_2)_3NH_2$ and the —$NH(CH_2)_2SH$ moieties of amifostine). According to one embodiment, the first portion of the molecule functions to align the molecule in close proximity to critical binding sites on nucleic acids and/or proteins, and the second portion of the molecule functions in a reaction that contributes to antiviral efficacy.

The above hypothesis for the mode of action of WR-1065 and related compounds is in part based upon several compounds have been found described to inhibit replication of multiple different families of viruses (Qian-Cutrone et al., 1996, Hamasaki and Ueno, 2001, Lacourciere et al. 2000, Li et al. 2001, Nishizono and Nair, 2000, Zang and Yen, 1999, Reddy et al. 1999, Xiao et al., 2001). These compounds were hypothesized to bind to and/or otherwise block post-transcriptional regulatory elements such as the REV response element (RRE) of HIV-1 or the PRE binding site of hepatitis B virus. These elements are required for export of viral mRNA from the nucleus to the cytoplasm, formation of viral proteins, and assembly of viral components. Some compounds are hypothesized to bind directly to the RRE or PRE; others are hypothesized to interfere with protein-RNA binding through indirect mechanisms. Most of the studied compounds were known to be structurally related to the broad category of cellular compounds known as polyamines and/or to have polyamine-like functions. Polyamines are ubiquitous, naturally occurring compounds found in all cells that are hypothesized to bind to DNA and RNA and to be involved in gene expression regulation; thus, the hypothesized mode of action for the antiviral effects of these agents is consistent with their structure and what is known about their naturally occurring counterparts. It should be noted that amifostine and its analogs differ significantly in structure from the above described compounds.

Variations to the chemical structure of the moiety —$(CH_2)_3NH_2$ may be tolerated without losing or altering the antiretroviral/antiviral efficacy of the compound, so long as the resulting structure retains a binding capacity/affinity that is similar to that observed with —$(CH_2)_3NH_2$ itself. Such variations may include more or less than three carbon atoms in the alkyl group, and a branched alkyl chain, lower alkyl substituents on the amino group. The potential importance of the moiety —$(CH_2)_3NH_2$ (or suitable variant) to antiviral effectiveness of the compounds of preferred embodiments is supported by the work of Laayoun et al., who demonstrated a significant increase in anti-mutagenic activity when cysteamine or WR-2721 is tethered to a chromophore (quinoline or acridine) that increases DNA binding (Laayoun et al. (1994), *Int J Radiat Biol* 66(3): 259-66). It is hypothesized that the antimutagenic activity of the aminothiols may result from a mode of action that is also relevant for their antiviral activity, suggesting that viral affinity could be altered by changing the chemical structure of the moiety —$(CH_2)_3NH_2$.

Gutschow et al. describe two compounds that are demonstrated to display significant antiretroviral/antiviral activity (Gutschow et al. (1995), *Pharmazie* 50(10): 672-5.). These compounds differ in structure considerably from the compounds of preferred embodiments, but the two most efficacious compounds have, as a portion of their structure, a cysteamine-like group. Gutschow et al. tested a number of compounds, some of which differed in the number of carbon atoms separating the sulfhydryl group and its adjacent amino group, and noted that the optimal antiviral effect was observed using molecules that had a cysteamine-like group and that this effect was diminished if the number of —$CH_2$— groups separating the sulfhydryl group and the first amino group was increased to three, as occurs in the aminothiols WR-151327 (chemical formula $CH_3NH(CH_2)_3NH(CH_2)_3SPO_3H_2$) and WR-151326 (chemical formula $CH_3NH(CH_2)_3NH(CH_2)_3SH$). Accordingly, altering the structure of the cysteamine-like group to include three —$CH_2$— groups between the sulfhydryl group and the amino group significantly reduced the capacity of the compound to function as an antiretroviral/antiviral agent.

In contrast to WR-151327 and WR-151326, other compounds of preferred embodiments have only two —$CH_2$— groups separating the sulfhydryl group from the first amino group, and thus possess superior antiretroviral/antiviral properties. The antiretroviral/activity of WR-1065 is significantly greater than that reported for WR-151326, and thus WR-1065 has functional capacities that are different from those of WR-151327 and WR-151326.

Significant questions remain as to how a molecule such as WR-1065 could interact with viral nucleic acids and proteins in such a way as to inhibit critical processes (such as replication, transcription, translation, or protein aggregation/functionality) without simultaneously exerting a similar effect upon cells of higher organisms. Some information from early work performed with viral genomes as models of DNA replication can be used to formulate testable hypotheses.

We hypothesize that for example, WR-1065 and its analogs interfere with critical components of the viral life cycle of many/all viruses through interactions with viral nucleic acids, nucleic acid-associated proteins, and/or molecular machines involved in nucleic acid and/or protein production and maintenance. We further hypothesize that fundamental differences in nucleic acid and protein production and maintenance of viruses versus higher organisms are responsible for the differential effects of WR-1065 and its analogs. The rationale for these hypotheses is supported by the following information.

Experimental evidence supports the hypothesis that the nucleic acids of higher organisms have a protein-to-DNA ratio of approximately 1:10. In contrast, the nucleic acids of many viruses, vegetative bacteriophage, and dinoflagellates have a protein-to-DNA ratio of approximately 1:1 (Cremisi, 1979; Kellenberger, 1988). The significantly higher ratio of proteins to nucleic acids of viruses would allow for enhanced interaction between proteins associated with nucleic acids, the nucleic acids themselves, and a molecule with nucleic acid and protein binding affinity. The enhanced opportunity for binding between WR-1065 and viral nucleic acids and proteins could result in deleterious effects upon viral nucleic acid production, maintenance, or functionality. A similar effect would not be expected to be exerted at the same magnitude upon the nucleic acids of higher organisms. The significantly lower ratio of proteins to nucleic acids in higher organisms versus viruses would be expected to reduce the opportunities for interaction/binding between WR-1065, nucleic acids, and adjacent proteins in higher organisms by a degree roughly comparable to the differences in the ratios of protein to nucleic acid found in these two different life forms.

In addition, there are considerable differences in the types and amounts of proteins associated with viral nucleic acids as opposed to the nucleic acids of higher organisms (Cremisi, 1979). These protein-based distinctions could result in further differences in the number or types of interactions between WR-1065 and components of viruses versus cellular components of higher organisms.

Other work suggests that WR-1065 could affect the functionality of molecular machines. For the purposes of illustration, only the molecular machines known as origin recognition complexes will be discussed, but the considerations presented below are applicable to many/all molecular machines of viruses versus higher organisms. Because the components and structure of these machines differ between simple life forms and higher life forms, WR-1065-associated effects could result in different consequences. The basis for this hypothesis comes from two separate areas of consideration. The replicon model as proposed by Jacob et al. in 1964 has been shown to be applicable to all bacterial replication systems as well as to several viral families, including simian virus-40 (SV-40). Bergsma et al. (1982) showed that initiation of replication in SV-40 required the interaction of a virally encoded initiator protein with a defined replicator sequence. In contrast to the study results, replication initiation-site selection within eukaryotic chromosomes is considered to be degenerate (Gilbert, 2004). For the latter chromosomes, multiple different replication initiation sites appear to exist, and no single obligatory site has been found.

Thus, it can be hypothesized that WR-1065 and similar compounds could block replication initiation through interactions with a defined replicator sequence on viral nucleic acids, while not exerting a similar effect upon the nucleic acids of higher organisms because of the degenerate nature of their initiation-site selection. Binding of WR-1065 to replication initiation sites of eukaryotic cells would be hypothesized to slow down nucleic acid processing and, hence, cell division, but not block it completely. This hypothesis is supported by the fact that WR-1065 has been shown to delay the progression of cells through the cell cycle, but the exact mechanism remains unclear.

Second, replication origin recognition complexes of higher animals share many similarities with analogous complexes in simple life forms, including viruses and archaeal cells (Gai et al., 2004). However, critical differences have been noted in the components and in the mode of action of these molecular machines (Gai et al., 2004). To use SV-40 as an example, the molecular machine known as the origin recognition complex consists of the oncogenic large tumor antigen that is formed as a monomer; six monomers then form a hexamer, and two hexamers assemble together, along with replication protein A, topoisomerase I, and polymerase-alpha/primase. These molecules form the replication initiation complex for SV-40. The functionality of this complex is highly dependent upon the conformation of individual monomers, as well as the conformation of the hexamer (Gai et al. 2004). The functionality of the entire replication initiation complex is also dependent upon the conformation of the target nucleic acids and the target initiation site (Gai et al., 2004). Because WR-1065 is known to have the capacity to alter the conformation of both nucleic acids and proteins, a complex such as that described for SV-40 would be especially vulnerable to induced conformational changes. Partial support for this hypothesis comes from studies demonstrating interactions between WR-1065 and topoisomerase enzymes. Analogous molecular machines that operate in cells of higher organisms would not be expected to share identical conformational requirements.

In addition, because origin recognition complexes of eukaryotic cells do not appear to require an origin of replication site, but rather are capable of using a variety of sites, it is reasonable to hypothesize that these latter origin recognition complexes could potentially tolerate a degree of conformational change that SV-40 and other virally-associated origin recognition complexes cannot tolerate.

All references cited herein, including but not limited to published and unpublished applications, patents, and literature references, as well as the references of the Appendix 1, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material. The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

APPENDIX 1

Allegra et al. (2002). "The ability of cystamine to bind DNA." *Amino Acids* 22(2): 155-66.

Bergamini et al. (1996). "In vitro inhibition of the replication of human immunodeficiency virus type 1 by beta-mercaptoethylamine (cysteamine)." *J Infect Dis* 174(1): 214-8.

Brekken et al. (1998). "Trypanosoma brucei gamma-glutamylcysteine synthetase. Characterization of the kinetic mechanism and the role of Cys-319 in cystamine inactivation." *J Biol Chem* 273(41): 26317-22.

Clark et al. (1997). "The aminothiol WR-1065 protects T-lymphocytes from ionizing radiation-induced deletions of the HPRT gene." *Cancer Epidemiol. Biomarkers and Prevention* 6:1033.

Cremisi, C. (1979). Chromatin replication revealed by studies of animal cells and papovaviruses (simian virus 40 and polyoma virus). *Microbiol Rev* 43(3): 297-319.

Gai, D., R. Zhao, D. Li, C. V. Finkielstein and X. S. Chen (2004). Mechanisms of conformational change for a replicative hexameric helicase of SV40 large tumor antigen. *Cell* 119(1): 47-60.

Grdina et al. (2000). "Amifostine: mechanisms of action underlying cytoprotection and chemoprevention." *Drug Metabol Drug Interact* 16(4): 237-79.

Gutschow et al. (1995). "[Bis((2,4-dioxo-1,2,3,4-tetrahydroquinazolin-3-yl)alkyl)disulfane and 3-(mercaptoalkyl)quinazolin-2,4(1H,3H)-dione: synthesis by ring transformation and antiviral activity. 42. Heterocyclic azines with heteroatoms in the 1- and 3-positions]." *Pharmazie* 50(10): 672-5.

Hamasaki et al. (2001). "Aminoglycoside antibiotics, neamine and its derivatives as potent inhibitors for the RNA-protein interactions derived from HIV-I activators." *Bioorg Med Chem Lett* 11(4):591-4.

Ho et al. (1995). "Cystamine inhibits HIV type 1 replication in cells of monocyte/macrophage and T cell lineages." *AIDS Res Hum Retroviruses* 11(4): 451-9.

Kalebic et al. (1994). "Organic thiophosphate WR-151327 suppresses expression of HIV in chronically-infected cells." *AIDS Research and Human Retroviruses* 10:727.

Kellenberger, E. (1988). About the □immer□ation of condensed and decondensed non-eukaryotic DNA and the concept of vegetative DNA (a critical review). *Biophys Chem* 29(1-2): 51-62.

Laayoun et al. (1994). "Aminothiols linked to quinoline and acridine chromophores efficiently decrease 7,8-dihydro-8-oxo-2'-deoxyguanosine formation in gamma-irradiated DNA." *Int J Radiat Biol* 66(3): 259-66.

Lacourciere et al. (2000). "Mechanism of neomycin and Rev peptide binding to the Rev responsive element of HIV-1 as determined by fluorescence and NMR spectroscopy." *Biochemistry* 39(19):5630-41.

Li et al. (2001). "A heterocyclic inhibitor of the REV-RRE complex binds to RRE as a □immer." *Biochemistry* 40(5): 1150-8.

List et al. (1997). "Stimulation of hematopoiesis by amifostine in patients with myelodysplastic syndrome." *Blood* 90(9): 3364-9.

Luedtke et al. (2003). "Fluorescence-based methods for evaluating the RNA affinity and specificity of HIV-1 Rev-RRE inhibitors." *Biopolymers* 70(1):103-19.

Newton et al. (1996). "Transport of aminothiol radioprotectors into mammalian cells: passive diffusion versus mediated uptake." *Radiat Res* 146(2):206-15.

Nguyen et al. (2003). "Amifostine and curative intent chemoradiation for compromised cancer patients." *Anticancer Research* 23:1649.

Nishizono et al. (2000). "Synthesis of biomimetic analogs of neomycin B: potential inhibitors of the HIV RNA Rev response element." *Nucleosides Nucleotides Nucleic Acids* 19(1-2):283-95.

North et al. (2002). "Restoration of wild-type conformation and activity of a temperature sensitive mutant of p53 (p53(V272M)) by the cytoprotective aminothiols WR1065 in the esophageal cancer cell line TE-1." *Mol. Carcinog.* 33(3): 181-8.

Oiry et al. (2004). "Synthesis and biological evaluation in human monocyte-derived macrophages of N—(N-acetyl-L-cysteinyl)-S-acetylcysteamine analogues with potent antioxidant and anti-HIV activities." *J Med Chem* 47(7): 1789-95.

Olsen et al. (1990). "Interaction of the human immunodeficiency virus type 1 Rev protein with a structured region in env mRNA is dependent on multimer formation mediated through a basic stretch of amino acids." *Genes Dev* 4(8):1357-64.

Perno et al. (1988). "Inhibition of HIF-1 replication in fresh and cultured human peripheral blood monocytes by azidothymidine." *J Experimental Medicine* 168:1111.

Qian-Cutrone et al. (1996). "Niruriside, a new HIV REV/RRE binding inhibitor from Phyllanthus niruri." *J Nat Prod* 59(2):196-9.

Rasey, J. S., N. J. Nelson, P. Mahler, K. Anderson, K. A. Krohn and T. Menard (1984). Radioprotection of normal tissues against gamma rays and cyclotron neutrons with WR-2721: LD50 studies and 35S-WR-2721 biodistribution. *Radiat Res* 97(3): 598-607.

Rasey, J. S., A. M. Spence, C. C. Badger, K. A. Krohn, D. M. Vera and J. C. Livesey (1988). Specific protection of different normal tissues. *Pharmacol Ther* 39(1-3): 33-43.

Reddy et al. (1999). "Inhibition of HIV replication by dominant negative mutants of Sam68, a functional homolog of HIV-1." *Rev Nat Med* 5(6):635-42.

Rossio et al. (1998). "Inactivation of HIV Type I infectivity with preservation of conformational and functional integrity of virion surface proteins." *Journal of Virology* 72:7992.

Santini et al. (1999). "The potential of amifostine: from cytoprotectant to therapeutic agent." *Haematologica* 84(11): 1035-42.

Schuchter, L. M. (1996). "Guidelines for the administration of amifostine." *Semin Oncol* 23(4 Suppl 8): 40-3.

U.S. Pat. No. 5,824,664 to Schein et al. "Suppression of HIV Expression by Organic Thiophosphate".

Xiao et al. (2001). "Inhibition of the HIV-I rev-RRE complex formation by unfused aromatic cations." *Bioorg Med Chem* 9(5):1097-113.

Zang et al. (1999). "Distinct export pathway utilized by the hepatitis B virus posttranscriptional regulatory element." *Virology* 259(2):299-304.

Zapp et al. (1997). "Modulation of the Rev-RRE interaction by aromatic heterocyclic compounds." *Bioorg Med Chem* 5(6):1149-55.

APPENDIX 2

| Viruses | Drug | Chemical Type | Target/Mode |
|---|---|---|---|
| Herpes virus | Vidarabine (Vira-A) | NRTI | Viral polymerase |
| | Acyclovir (Zovirax) | NRTI | Viral polymerase |
| | Famcylovir (Famvir) | | |
| | Idoxuridine (Herplex liquifilm, stoxil) | | Viral polymerase |
| | Trifluridine (Viroptic) | | Inhibitor of thymidylate synthetase |
| | Tromantadine | Derivate of adamantane | Inhibits viral replication |
| | Penciclovir (Denavir) | | Interferes with enzymes for viral replication |
| | Docosanol (Abreva) | Long chain alcohol | Changes cell membrane of healthy cells |
| | Valacyclovir (Valtrex) | | |
| | Imiquimod (Aldara) | | |
| Cytomegalo virus | Gancyclovir (Cytovene) | NRTI | Viral polymerase |
| | Valganciclovir (Valcyte) | NRTI | Viral polymerase |
| | Fomivirsen (Vitravene, ISIS 2922) | Antisense oligonucleotide | Prevents production of viral protein |
| | Foscarnet (Foscavir) | | |
| | Cidofovir (Vistide, HPMPC) | NRTI | Viral polymerase |
| Retrovirus | Zidovudine (AZT) | NRTI | Reverse transcriptase |
| | Didanosine (ddI) | NRTI | Reverse transcriptase |
| | Zalcitabine (ddC) | NRTI | Reverse transcriptase |
| | Stavudine (d4T) | NRTI | Reverse transcriptase |
| | Lamivudine (3TC) | NRTI | Reverse transcriptase |
| | Abacavir (ABC) | NRTI | Reverse transcriptase |
| | Emtricitabine (Emtriva, FTC) | NRTI | Reverse transcriptase |
| | Tenofovir (Viread) | NRTI | Reverse transcriptase |
| | Enfuvirtide (Fuzeon, T-20) | | Binds to HIV envelope glycoprotein gp41 prevents viral fusion with |
| | Nevirapine (Viramune) | NNRTI | Reverse transcriptase |
| | Delavirdine (Resciprtor) | NNRTI | Reverse transcriptase |
| | Efavirenz (Sustiva) | NNRTI | Reverse transcriptase |
| | Saquinavir (Invirase) | Peptide analog | Protease inhibitor |

-continued

| Viruses | Drug | Chemical Type | Target/Mode |
|---|---|---|---|
| | Ritonavir (Norvir) | Peptide analog | Protease inhibitor |
| | Indinavir (Crixivan) | Peptide analog | Protease inhibitor |
| | Nelfinavir (Viracept) | Peptide analog | Protease inhibitor |
| | Amprenavir (Agenerase, VX-478, 141W94) | Peptide analog | Protease inhibitor |
| | Lopinavir (Kaletra) | Peptide analog | Protease inhibitor |
| | Atazanavir (Reyataz) | Peptide analog | Protease inhibitor |
| | Tipranavir (Aptivus) | Peptide analog | Protease inhibitor |
| | Fosamprenavir (Lexiva) | Peptide analog | Protease inhibitor |
| Influenza virus | Thiovir | Adventrx pharmaceuticals: influenza A and avian/human influenza virus Thiophosphonoformates | |
| | Amantadine (Symmetrel) | Influenza A strains: tricyclic amine | Matrix protein/haemagglutinin |
| | Rimatadine (Flumadine) | Influenza A strains: tricyclic amine | Matrix protein/haemagglutinin |
| | Zanamivir (Relenza) | Influenza A and B strains: neuraminic acid mimetic | Neuraminidase inhibitor |
| | Oseltamivir (Tamiflu, GS4104) | Influenza A and B strains: neuraminic acid mimetic | Neuraminidase inhibitor |
| | Peramivir (BCX-1812, RWJ270201) | Influenza A and B strains | |
| Hepatitis | FDA approved (below) | | |
| | Adefovir dipivoxil (Preveon) | NRTI | Reverse transcriptase |
| | Interferon alfa-2a (Roferon) | Protein | Activates cell defense proteins |
| | Interferon alfa-2b (Intron-A) | Protein | Activates cell defense proteins |
| | Interferon alfa-n3 (Alferon) | Protein | Activates cell defense proteins |
| | Interfernon alfacon (Infergen) | Protein | Activates cell defense proteins |
| | Peginterferon alfa-2a (PEG-Intron) | Polyethylene glycol | |
| | Peginterferon alfa-2b (Pegasys) | Polyethylene glycol | |
| | FDA approved vaccines | | |
| | Hepatitis A | | |
| | Hepatitis A and B | | |
| | Hepatitis B immune globulin | | |
| | Hepatitis B | | |
| | Hepatitis B and Haemophilus influenza type b polysaccharide conjugate | | |
| Hep B | Investigational drugs (below) | | |
| | BAM-205 (NOV-205) | | |
| | Clevudine (L-FMAU) | Pyrimidine analog | |
| | Elvucitabine (ACH-126, 443, BetaL-Fd4C) | NRTI | Reverse transcriptase |
| | Telbivudine (L-deoxythymidine, LdT) | NRTI | Suppresses viral replication--polymerase |
| | Entecavir (Baraclude) | NRTI | Suppresses viral replication |
| | HepeX-B | Monoclonal antibodies | Polymerase inhibitor |
| | Pradefovir (Remofovir) | | |
| | Valtorcitabine (Val-LdC) | Valine ester | Inhibits replication |
| | HE2000(Immunitin) | Alph-epibromide | Immune regulating hormone |
| | Zadaxin (Thymalfasin) | Amino acid peptide | Stimulates immune system |
| Hep C | Investigational drugs (below) | | |
| | AbXTL68 (XLT6865) | Monoclonal antibody | |
| | NS5B | RNA polymerase | Inhibits viral polymerase |
| | MN283 | | |
| | MN107 | | |
| | BILN-2061 | | Protease inhibitor |
| | FK788 | Leflunomide analog | |
| | HepeX-C | Monoclonal antibodies | |
| | Histamine dihydrochloride (Ceplene) | Histamine | |
| | Interferon gamma-1b (Actimmune) | Protein | Anti-fibrotic |
| | Isatoribine (ANA245) | NRTI | Polymerase inhibitor |
| | ISIS 14803 | Phosphorothioate antisense oligonucleotide | Inhibits replication and protein expression |

| Viruses | Drug | Chemical Type | Target/Mode |
|---|---|---|---|
| | Levovirin (LVV) | L-enantiomer of ribavirin--NRTI | |
| | Merimempodib (VX-497) | Phenyloxazole derivative | IMPDH inhibitor |
| | Mycophenolate mofetil (Cellcept) | | Immunosuppressive drug |
| | Thymosin alpha 1 (TA1) | Synthetic peptide | Increases T cell function |
| | Viramidine (ICN3142) | Amidine prodrug of ribavirin--NRTI | |
| | ANA971 | Prodrug of isatoribine | |
| | ANA245 (Isatoribine) | | |
| | REBIF | Beta interferon | |
| | Infergen/Consensus | Interfernon | |
| | Oral Interferon alpha | | |
| | IP-501 | Oral phospholipids antifibrotics | |
| | ANA975 | Prodrug of isatoribine | |
| | EMZ702 | | |
| | Rituximab (Rituxan, Mabthera) | Anti-CD20 monoclonal antibody | |
| | NM283 (Valopicitabine) | | Polymerase (RdRp) inhibitor |
| | HCV/MF59 | | Enhances immune response |
| | SCH-6 | | Serine protease inhibitor |
| | HCV-796 | Non-nucleoside | Polymerase inhibitor |
| | Civacir (Hepititis C Immune Globulin) | Polyclonal antibody | |
| | E-1 | Prostaglandins—therapeutic vaccine | |
| | Tarvacin | Anti-phosphotidylserine | Stimulates immune defense |
| | JTK 103 | | Protease inhibitor |
| | AVI-4065 (Neugene) | Phosphorodiamidate morpholion oligomer | |
| | Omega Interferon | | |
| | Multiferon | Multi-subtype natural human alpha interferon | |
| | Alinia (nitrazoxanide) | Thiazolides | |
| | IDN-6556 | | Capase inhibitor |
| | Albuferon | Fusion protein interferon alpha-albumin | |
| | Medusa Interferon | Long acting interferon | |
| | IC41 | Therapeutic vaccine | |
| | VX 950 | | Protease inhibitor (NS3-4A) |
| | CPG 10101 (Actilon) | | Immunomodulator |
| | BIVN-401 (Virastat) | Monoclonal antibodies | |
| | MX-3253 (Celgosivir) | Prodrug of castanospermine | Alpha-glucosidase I inhibitor |
| | SCH 503034 | | Inhibits serine protease |
| | HCV-AB68 | | |
| | HCV-MF59 | | |
| | Actilon | Synthetic oligonucleotide | Selective TLR9 agonist |
| | Enbrel | Anti-tumor necrosis factor alpha | |
| | BLX-883 | Locteron-interferon | |
| | AVI-4065 | | |
| | HCV-086 | | |
| | R803 | Non-nucleoside | Polymerase inhibitor |
| | Interleukin-10 | | Anti-fibrotic |
| | Heptazyme | | RNA inhibitor |
| Rhinovirus | Rupintrivir (AG7088) | Pfizer Inc: Experimental - - - | Protease inhibitor |
| | BTA-798 | Biota: Experimental - - - | |
| | MRL-2471 | | |
| Rhinovirus/ Picornavirus | Pleconaril | | Blocks attachment and uncoating |

-continued

| Viruses | Drug | Chemical Type | Target/Mode |
|---|---|---|---|
| Picornavirus/ Poliovirus | WIN51711 | | Bind to viral capsid to prevent uncoating |
| Broad Spectrum | WIN Rep9 | | |
| | Ampligen | | |
| | Ribaviran (Rebetol, Rebetron) | Triazol carboxamide | RNA mutagen/ IMPDH inhibitor |

What is claimed is:

1. A method of inhibiting replication of Orthomyxoviridae viruses in an individual in which the virus occurs, the method comprising:
    selecting an individual having an Orthomyxoviridae viral infection, wherein the selected individual is not infected with HIV;
    administering to the selected individual an effective antiviral amount of a compound or a pharmaceutically acceptable salt or solvate thereof, wherein the compound has a formula of Formula (I):

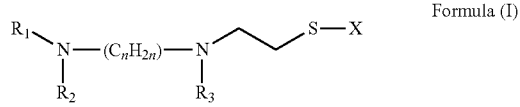

Formula (I)

wherein X is selected from the group consisting of —$PO_3H_2$, hydrogen, acetyl, isobutyryl, pivaloyl, and benzoyl,
wherein each of $R_1$, $R_2$, and $R_3$ is hydrogen
wherein n is 3, and
wherein the antiviral amount is not greater than the oral radioprotective dosage of the compound.

2. The method of claim 1, wherein X is —$PO_3H_2$.
3. The method of claim 1, wherein X is hydrogen.
4. The method of claim 1, wherein the compound is administered to the selected individual at a daily dosage of from about 200 to about 3000 milligrams per square meter of body surface area.
5. The method of claim 1, wherein the compound is administered by a method selected from the group consisting of orally administering, intravenously administering, parenterally administering, subcutaneously administering, and administering by inhalation.
6. The method of claim 1, wherein the compound is selected from the group consisting of amifostine, the free thiol form of amifostine, and a combination of both amifostine and the free thiol form of amifostine.
7. The method of claim 1, wherein the antiviral amount is not greater than about 4.25 millimoles per square meter of body surface area.
8. The method of claim 1, wherein the compound is administered to the individual on a daily basis in an amount not greater than about 1.6 millimoles per square meter of body surface area per day.
9. The method of claim 1, wherein the antiviral amount is not greater than about 113 micromoles per kilogram of body weight.
10. The method of claim 1, wherein the individual is a human.
11. The method of claim 1, wherein the virus is an influenza virus.
12. The method of claim 11, wherein the influenza virus is a type selected from the group consisting of HINI and H3N2.
13. The method of claim 1, wherein the compound is not administered in combination with any other antiviral agent.
14. The method of claim 1, wherein X is acetyl.
15. The method of claim 1, wherein X is isobutyryl.
16. The method of claim 1, wherein X is pivaloyl.
17. The method of claim 1, wherein X is benzoyl.

* * * * *